United States Patent [19]

Oishi et al.

[11] Patent Number: 4,948,250
[45] Date of Patent: Aug. 14, 1990

[54] ATOMIC ABSORPTION SPECTROPHOTOMETER

[75] Inventors: Konosuke Oishi, Mito; Hideaki Koizumi; Masataka Koga, both of Katsuta, all of Japan

[73] Assignee: Hitachi, Ltd., Tokyo, Japan

[21] Appl. No.: 621,464

[22] Filed: Jun. 18, 1984

[30] Foreign Application Priority Data

Jun. 16, 1983 [JP] Japan ............................. 58-108911

[51] Int. Cl.⁵ .............................................. G01J 3/42
[52] U.S. Cl. ................................................... 356/307
[58] Field of Search ............... 356/307, 319, 320, 323, 356/325

[56] References Cited

U.S. PATENT DOCUMENTS 4,299,485  11/1981  Barlow et al. ....................... 356/307
4,357,673  11/1982  Willis et al. ...................... 356/323 X

OTHER PUBLICATIONS

Koizumi et al., *Analytical Chemistry*, vol. 49, No. 8, Jul. 1977, pp. 1106–1112.

Primary Examiner—F. L. Evans
Attorney, Agent, or Firm—Antonelli, Terry, Stout & Kraus

[57] ABSTRACT

In atomic absorption spectrophotometers such as Zeeman atomic absorption spectrophotometer, the present invention is characterized in that the correction timing of background absorption in sample light is made to coincide with that of reference light so as to improve the accuracy of the output signals of the spectrophotometer. To accomplish this object, the present invention constitutes a calculation processing unit for storing and calculating signals by means for separating one signal consisting of sample signals and reference signals applied thereto from amplification means for amplifying photoelectrically converted signals into sample and reference signals, and storing them, means for calculating respectively the mean values of two time adjacent signals of one of the sample and reference signals to prepare a signal of the mean values, and means for calculating the difference of the logarithmic converted values of the signals of the other of the sample and reference signals and those of the signals of the signal of the mean values at the same points of time, and obtaining correction signals of background absorption.

5 Claims, 5 Drawing Sheets

ATOMIC ABSORPTION SPECTROPHOTOMETER

BACKGROUND OF THE INVENTION

This invention relates to an atomic absorption spectrophotometer which improves the accuracy of calculation output signals.

In atomic absorption spectrophotometers in general, absorption of light other than by an atom to be analyzed, that is so-called "background absorption", occurs, and hence the accuracy of of signals drops.

Background absorption includes scattering of light by fine particles and absorption of light by molecular gas, for example, and they are factors that cause measurement error of the spectrophotometer. Accordingly, the atomic absorption spectrophotometers are generally equipped with a function of correcting the background absorption.

The atomic absorption spectrophotometers having such a correction function of the background absorption are known, for example, from the magazine "Analytical Chemistry", Vol. 49, No. 8, July, 1977, p.p. 1106–1112.

The conventional systems such as described above involve the problem that the measurement with a high level of accuracy can not be made because the absorbancies due to the background absorption in sample light and reference light are compared with each other at different detection timings so as to detect output signals.

SUMMARY OF THE INVENTION

With the background described above, the present invention is directed to provide an atomic absorption spectrophotometer which can eliminate the adverse influences by background absorption and can therefore improve the calculation accuracy.

The atomic absorption spectrophotometer in accordance with the present invention is characterized in that a calculation processing unit for storing and calculating signals is constituted by means for separating one signal system consisting of sample signals and reference signals applied thereto from amplification means for amplifying photoelectrically converted signals into a sample signal system and a reference signal system, and storing them, means for respectively calculating the mean values of two adjacent signals in one of the sample and reference signal systems to prepare a signal system of the mean values, and means for calculating the difference of the logarithmic canverted values of the signals of the other of the sample and reference signal systems and those of the signals of the signal system of the mean values at the same timing, and obtaining correction signals of background absorption.

DESCRIPTION OF THE PREFERRED EMBODIMENTS

Figure 1:
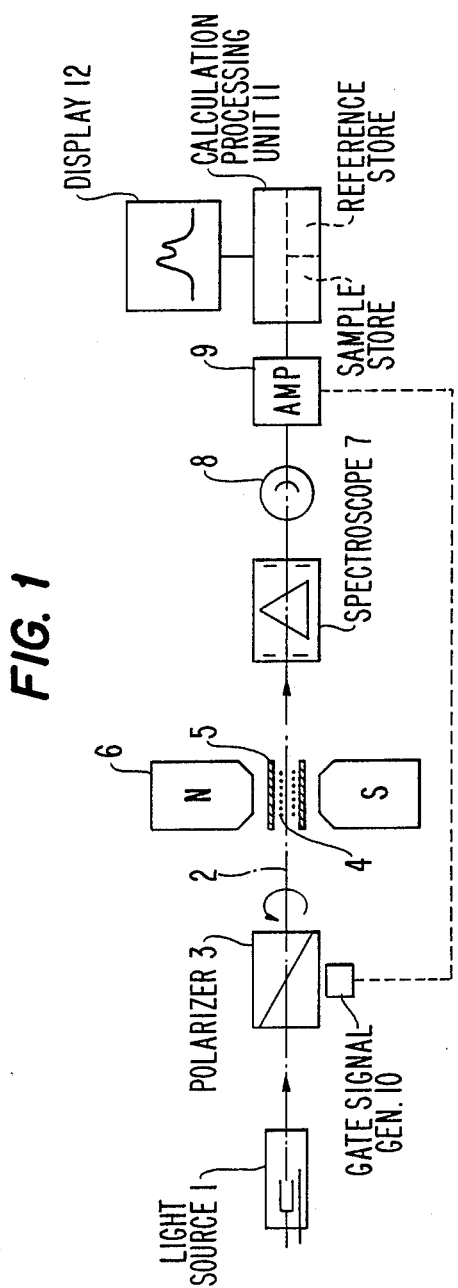
FIG. 1 is a block diagram showing a spectrophotometer to which the present invention is applied.

In FIG. 1, reference numeral 1 represents a light source for emitting sample light, which is absorbed by an atom to be analyzed, and reference light which is not absorbed by the atom. A so-called "hollow cathode lamp" using a material containing the same element as the element to be analyzed in a discharge cathode is generally used as the light source. Reference numeral 2 represents linearly polarized light generated when the light emitted from the light source 1 is linearly polarized by a polarizer 3. The polarizer 3 linearly polarizes the incident natural light, and the polarization plane of the linearly polarized light is perpendicular to the travelling direction of the light 2. In other words, the direction of the magnetic field spectrum when the linearly polarized light is regarded as an electromagnetic wave is perpendicular to the travelling direction of the light 2. The polarizer 3 rotates at a predetermined number of revolution with the travelling direction of the light as its axis. Accordingly, the polarization plane of the linearly polarized light after passing through the polarizer 3 (magnetic field spectrum) also rotates.

Reference numeral 4 represents the gas (vapor) of the atom to be analyzed, and reference numeral 5 does a heating furnace which heats the material to be analyzed to a high temperature of from 2,000° to 3,000° C., decomposes thermally the material and vaporizes the solid material. Reference numeral 6 represents a magnet which applies a magnetic field of about 10,000 Gauss to the vapor of the atom 4 to be analyzed, and the direction of the magnetic field is perpendicular to the travelling direction of the light 2.

Reference numeral 7 represents a spectroscope, which selectively takes out the wavelength of the atomic resonance absorption line of the atom to be analyzed from various emission spectra emitted from the light source 1. Reference numeral 8 represents a photoelectric conversion element, and reference numeral 9 does an amplifier.

Reference numeral 10 represents a gate signal generator, which detects the angle of rotation (phase of rotation) of the polarizer 3, and applies its electric signal to the amplifier 9. Reference numeral 11 represents a calculation processing unit, which stores and calculates the optical signals, and reference numeral 12 does a display, which displays the result of calculation of the optical signals.

The following two kinds of relation exist between the atom 4 to be analyzed and the incident linearly polarized light 2 due to the Zeeman effect:

(1) When the direction of oscillation of the incident linearly polarized light (direction of the magnetic field spectrum) is in agreement with the direction of the field of the magnet 6, the atom 4 to be analyzed absorbs the linearly polarized light 2 most strongly.

(2) When the direction of oscillation of the linearly polarized light 2 is perpendicular to the direction of the magnetic field, the atom 4 to be analyzed does not absorb this linearly polarized light 2.

In other words, the ratio of the absorption of the incident linearly polarized light by the atom, which is placed inside the magnetic field, is proportional to $(\cos \omega t)^2$ where $\omega t$ represents the angle between the direction of the magnetic field vector of the linearly polarized light and the direction of the magnetic field applied to the atom. Incidentally, the absorption of the polarized light due to the Zeeman effect will be described briefly. In short, in the apparatus shown in FIG. 1, the sample light S absorbed by the atom 4 to be analyzed and the reference light R not absorbed by the atom 4 are provided. Actual measurement is carried out in the following way. When cadmium in soil is to be analyzed, for example, a predetermined quantity of soil weighed in advance is introduced into the heating furnace 5, and cadmium contained in the soil is vaporized to vapor inside the heating furnace 5. Organic matters contained in the soil are turned into ash in this case, and fine particles (smoke or soot) of carbon are generated. As the linearly polarized light 2 passes inside the heating furnace 5, the sample light S is absorbed by the cadmium atom but the reference light R is not. However, both rays of light are equally scattered by the fine carbon particles and the like, and their intensity is decreased. This rotation can be numerically expressed as follows:

$$S = S_0 \cdot \exp(-A-B) \tag{1}$$

$$R = R_0 \cdot \exp(-B) \tag{2}$$

where:
$S_0$: intensity of incident sample light to heating furnace 5
S: intensity of transmitted light of sample light from heating furnace
$R_0$: intensity of incident reference light to heating furnace 5
R: intensity of transmitted light of reference light from heating furnace 5;
A: absorbancy of light by cadmium atom
B: absorbancy of background absorption (apparent absorption by scatter of light and the like)

Since the absorbancy A is proportional to the number N of cadmium atoms, it can be expressed by the following equation:

$$A = N \cdot F_0 \tag{3}$$

where $F_0$: constant determined by the kind of atom and structure of heating furnace 5.

In the apparatus shown in FIG. 1, the electric signals corresponding to equation (1) and (2) are delivered to the calculation processing unit 11 so as to determine the absorbancy A. In this case, the constant $F_0$ is determined by introducing in advance a predetermined quantity of cadmium standard sample into the heating furnace 5. In this manner, the required number N of cadmium atoms is determined by generally introducing an unknown quantity of sample such as soil into the heating furnace to measure its absorbancy A, and then calculating the signals.

Correction of background absorption is carried out in the following manner. First, the logarithmic values on both sides of each equation (1) and (2) are obtained as follows:

$$\text{Log } S = \text{Log } S_0 - A - B \tag{4}$$

$$\text{Log } R = \text{Log } R_0 - B \tag{5}$$

Assuming that the apparatus is arranged so that the intensity of the incident light $S_0$ is equal to that of the incident light $R_0$, the difference between equation (4) and (5) can be given as follows:

$$\text{Log } S - \text{Log } R = \text{Log } S_0 - \text{Log } R_0 - A = -A \tag{6}$$

In the manner described above, the absorbancy B of background absorption can be eliminated and the absorbancy A due to the cadmium atoms alone can be obtained.

The correction method described above is a typical example of the methods of correction the background absorption of an atomic absorption spectrophotometer utilizing the Zeeman effect. However, correction can also be made by other methods by generating generally two optical signals S and R corresponding to the sample light and the reference light, respectively. In any of these methods, it is necessary to eliminate the absorbancy B by conducting the subtraction between both signals as expressed by equation (6).

Figure 2:
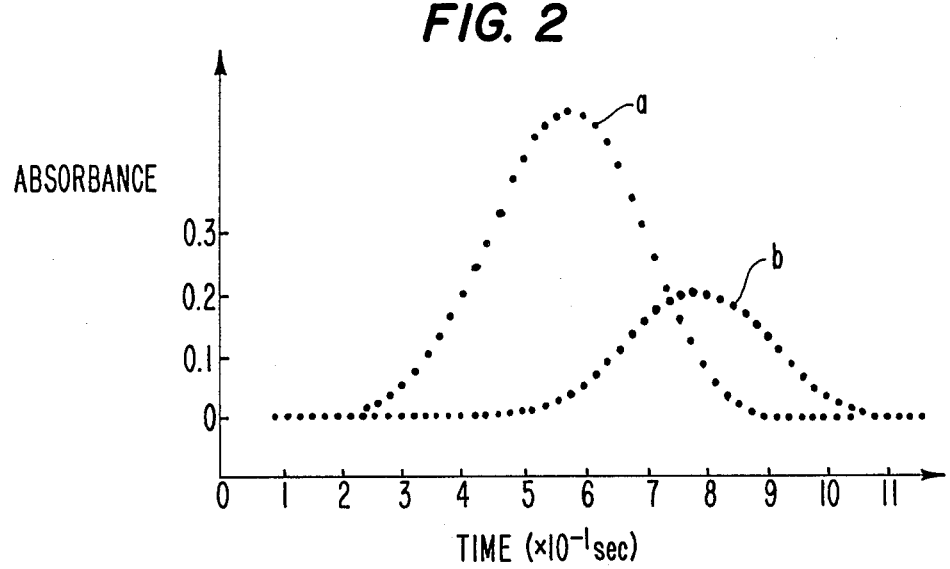
FIGS. 2 through 5 are diagrams, each useful for explaining the operation of the present invention.

When a predetermined quantity of soil sample is introduced, for example, into the heating furnace 5 of the apparatus shown in FIG. 1, various organic matters contained in the soil are first ashed, and smoke, soot, and the like generated. Then, cadmium as the atom to be analyzed contained the soil is vaporized. FIG. 2 shows the change with time of the absorbancy A of the cadmium atom and the absorbancy B by background absorption by the smoke, soot, and the like. In the diagram, symbol a represents the absorbancy [signal B(t)] due to background absorption, and b does the absorbancy [signal A(t)] due to the absorption by the atoms. Incidentally, it is not possible in the actual apparatus to independently measure the absorbancy A by the cadmium atoms and the absorbancy B due to background absorption, and hence FIG. 2 imaginarily represents the relation for the purpose of explaining the phenomenon.

Figure 3:
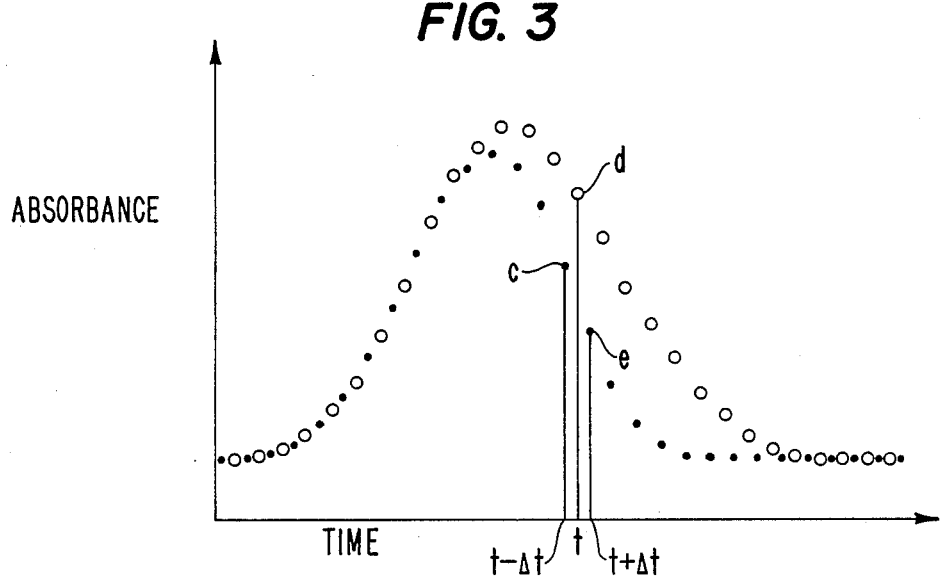

FIG. 3 is a diagram showing the signals obtained in the actual apparatus. In the diagram, symbol c represent a reference signal [$R(t-\Delta t)$] at a time $(t-\Delta t)$, d is a sample signal [$S(t)$] at a time t, and e is a reference signal [$R(t+\Delta t)$] at a time $(t+\Delta t)$. The reference signal and the sample signal are obtained as the dotted line with the passage of time for the following reason.

In FIG. 1, the sample signal S(t) and the reference signal R(t) are obtained when the oscillation plane of the linearly polarized light 2 becomes parallel to the direction of the magnetic field due to the rotation of the polarizer 3, and when it becomes perpendicular to the latter, respectively. Accordingly, both signals can not be obtained at the same point of time, but can be obtained in the following sequence in accordance with the time t in synchronism with the rotation of the polarizer 3.

$$\ldots, S(t-2\Delta t), R(t-\Delta t), S(t), R(t+\Delta t), S(t+2\Delta t), \ldots$$

Accordingly, equation (1) and (2) can be rewritten as follows in consideration of the time t:

$$S(t) = S_0 \cdot \exp[-A(t) - B(t)] \tag{7}$$

$$R(t-\Delta t) = R_0 \cdot \exp[-B(t-\Delta t)] \tag{8}$$

Alternatively, $$S(t) = S_0 \cdot \exp[-A(t) - B(t)] \tag{9}$$

$$R(t+\Delta t) = R_0 \cdot \exp[-B(t+\Delta t)] \tag{10}$$

Incidentally, since A(t) and B(t) change with the time t as shown in FIG. 3, the value of the absorbancy B(t) and that of the absorbancy $B(t \pm \Delta t)$ due to the background absorption in the sample and reference signals obtained at the different points of time, respectively, are not equal to each other. Accordingly, it has been found that the value of the absorbancy B(t) due to the background absorption can not be correctly eliminated using equation (7) and (8) or (9) and (10).

In the atomic absorption spectrophotometer having the construction shown in FIG. 1, the present invention divides the sample signals and the reference signals, i.e., ..., $S(t-2\Delta t)$, $R(t-\Delta t)$, $S(t)$, $R(t+\Delta t)$, $S(t+2\Delta t)$, ... into the following two signal systems X and Y by the gate signal generator 10, and stores them in the memory portion of the calculation processing unit 11:

X: ..., $S(t-2\Delta t)$, $s(t)$, $S(t+2\Delta t)$, ...
Y: ..., $R(t-\Delta t)$, $R(t+\Delta t)$, $R(t+3\Delta t)$, ...

Next, an imaginary reference signal R(t), which corresponds to the time of measurement of the sample signal S(t), is calculated in accordance with equation below, though the time of measurement of S(t) is not in agreement with that of $R(t+\Delta t)$:

$$R(t) = \frac{R(t - \Delta t) + R(t + \Delta t)}{2} \quad (11)$$

Figure 5:
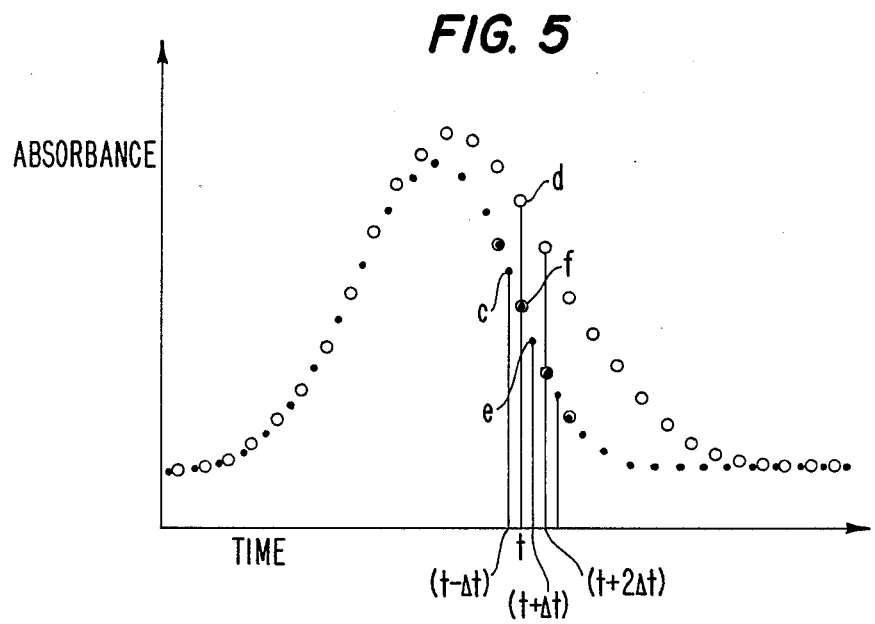

After the calculation is made as described above, the absorbancy of FIG. 3 becomes such as shown in FIG. 5. In the diagram, symbol f represents new data R(t), and this corresponds to the data obtained at the intermediate time t between two signals $R(t-\Delta t)$ and $R(t+\Delta t)$ at c and e, and becomes a reference signal at the same time as the time of measurement t of the simple signal S(t) of d.

When the calculation of equation (11) is applied to the signal system Y described above, the following new signal system Y' can be obtained.

Y': ..., $R(t - 2\Delta t)$, $R(t)$, $R(t + 2\Delta t)$, ...

Using the new signal system Y', $$S(t) = S_o \cdot \exp[-A(t) - B(t)] \quad (12)$$

$$R(t) = R_o \cdot \exp[-B(t)] \quad (13)$$

with the previso that $$B(t) = \frac{B(t - \Delta t) + B(t + \Delta t)}{2}$$

Here, since the absorbancy B(t) due to the background absorption can be regarded as changing linearly between the time $(t-\Delta t)$ and the time $(t+\Delta t)$, it is possible to put B(t)=B(t).

Figure 4A:
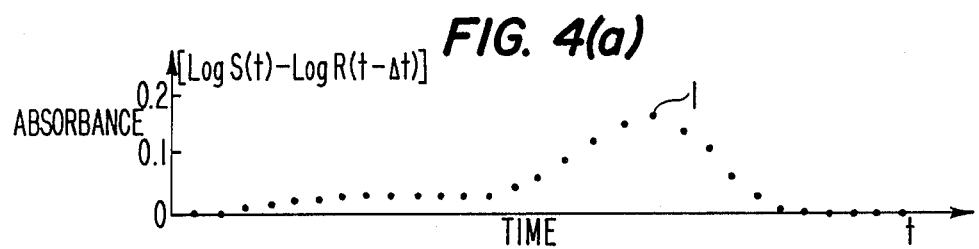
Figure 4B:
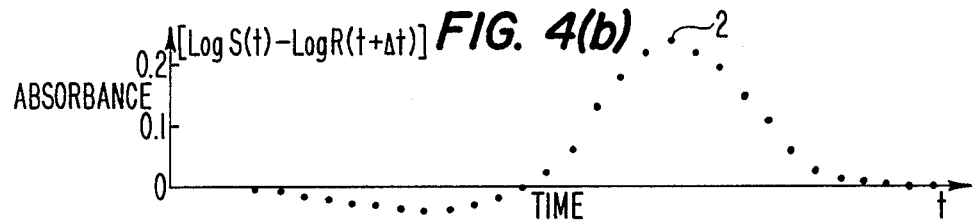
Figure 4C:
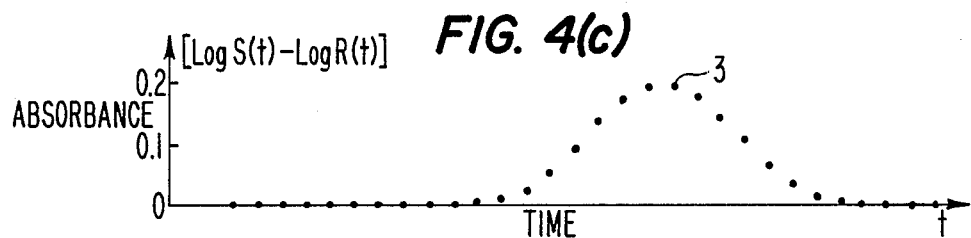

Next, the logarithmic values are obtained for both sides of equation (12) and (13), and B(t) is removed from them. The background correction signal obtained in this manner is shown in FIG. 4(c). FIG. 4(a) shows the absorbancy which is calculated in accordance with equation (7) and (8) without recognizing the difference of absorbancy at different timings, and FIG. 4(b) shows the absorbancy calculated in accordance with equation (9) and (10) without recognizing likewise the difference. In these cases, a positive or negative error of correction occurs on the left with respect to the position of the maximum value of the corrected signal, respectively. Such a positive or negative error of correction does not at all occur in the case of FIG. 4(c). In other words, a background correction signal which is extremely approximate to the true atomic absorption signal of cadmium shown in FIG. 2(b) can be obtained.

As described above, the imaginary reference signal is obtained by making the points of time of measurement agree with each other in accordance with equation (11), and background correction is then made using the signal system Y' in place of the signal system Y described already and the signal system X in accordance with equation (12) and (13). Accordingly, the error of background correction can be markedly reduced. Such calculation processing can be made when the processing such as shown in FIG. 6 is carried out in the calculation processing unit 11.

Incidentally, in the embodiment described above, the imaginary reference signal is calculated in accordance with equation (11), but the same result could be obtained when an imaginary sample signal corresponding to the time of measurement of the sample signal is calculated.

What is claimed is:

1. An atomic absorption spectrophotometer which comprises:

a light source for emitting sample light absorbed by an atom to be analyzed and reference light not absorbed by said atom;

radiation means for sequentially radiating said two kinds of light to an analysis sample with a predetermined time interval;

photoelectric conversion means for photoelectrically converting the light passing through said analysis sample; and calculation processing means for separating the electric signals from said photoelectric conversion means into a sample signal and a reference signal, and for calculating the absorbency from approximate mean values of two time adjacent signals of one of said sample signals and said reference signals, and from the signals of the other of said sample signals and said reference signals at the same time as said mean values.

2. The atomic absorption spectrophotometer as defined in claim 1 wherein said calculation processing means includes means for storing separately said sample signals and said reference signals.

3. The atomic absorption spectrophotometer as defined in claim 1 wherein said calculation processing means calculates the absorbancy from the difference between a converted logarithmic value of said approximate mean value and that of the signal at the same time as said mean value.

4. The atomic absorption spectrophotometer as defined in claim 1, wherein said radiation means includes rotary polarizer means.

5. An atomic absorption spectrophotometer which comprises:

a light source for emitting sample light absorbed by an atom to be analyzed and reference light not absorbed by said atom;

rotary polarizer means for sequentially radiating said two kinds of light to analysis sample with a predetermined time interval;

photoelectric conversion means for photoelectrically converting the light passing through said analysis sample;

amplification means for amplifying the electric signals from said photoelectric conversion means;

gate signal generation means for sensing the rotating position of said rotary polarizer means to generate a signal discriminating said sample light from said reference light, and for applying said discrimination signal to said amplification means; and calculation processing means for separating one signal consisting of said sample signals and said reference signals applied thereto from said amplification means into a sample signal and a reference signal, storing therein said sample and reference signals, calculating respectively the mean values of two time adjacent signals in one of said sample and reference signals to prepare a signal of said mean values, and calculating the difference between the logarithmic values of the signals in the other of said sample and reference signals and those of the signals in said signal of said mean values at the same points of time, respectively, to obtain a correction signal of background absorption.

* * * * *